US005493109A

United States Patent [19]
Wei et al.

[11] Patent Number: 5,493,109
[45] Date of Patent: Feb. 20, 1996

[54] OPTICAL COHERENCE TOMOGRAPHY ASSISTED OPHTHALMOLOGIC SURGICAL MICROSCOPE

[75] Inventors: Jay Wei, Fremont; Thomas Hellmuth, Danville, both of Calif.

[73] Assignee: Carl Zeiss, Inc., Thornwood, N.Y.

[21] Appl. No.: 292,433

[22] Filed: Aug. 18, 1994

[51] Int. Cl.$^6$ ...................................................... G02B 7/09
[52] U.S. Cl. ......................................... 250/201.3; 606/10
[58] Field of Search ............................ 250/201.2, 201.3; 606/4, 5, 10, 11

[56] References Cited

U.S. PATENT DOCUMENTS

| | | | |
|---|---|---|---|
| 4,512,642 | 4/1985 | Ito et al. | 354/4 |
| 4,685,140 | 8/1987 | Mount, II | 382/6 |
| 4,880,001 | 11/1989 | Weinberg | 606/11 |
| 4,994,058 | 2/1991 | Raven et al. | 606/5 |
| 5,098,426 | 3/1992 | Sklar et al. | 606/5 |
| 5,288,987 | 2/1994 | Vry et al. | 250/201.3 |
| 5,359,417 | 10/1994 | Müller et al. | 356/375 |

OTHER PUBLICATIONS

David Huang, "Optical Coherence Tomography", Massachusetts Institute of Technology, May 1993.
Measurement of Corneal Thickness by Low–Coherence Interferometry by C. K. Hitzenberger, *Applied Optics*, vol. 31, No. 31, Nov. 1992, pp. 6637–6642.
New Equipment and Methods for Determining the Contour of the Human Cornea by M. G. Townsley, *Contacto*, 11(4), 1967, pp. 72–81.
Accuracy and Precision of Keratometry, Photokeratoscopy, and Corneal Modeling on Calibrated Steel Balls by M. C. Gemmill, M. J. Lynn, and A. Nizam in *Arch. Ophthalmol.*, vol. 107, Aug. 1989, pp. 1235–1239.
Optical Coherence Tomography by Huang et al., *Science*, 254, Nov. 22, 1991 pp. 1178–1181.
Intraoperative Raster Photogrammetry—the PAR Corneal Topography System by M. W. Berlin, *J. Cataract Retract Surg.* vol. 19, Suppl. 1993, pp. 188–192.
Micron Resolution Imaging of the Anterior Eye in Vivo with Optical Coherence Tomography by J. A. Izatt et al. 1994 pp. 1–24.
Micron–Resolution Ranging of Cornea Anterior Chamber by Optical Reflectometry by D. Wang, J. Wang, C. P. Lin, C. A. Puliafito, and J. G. Fujimoto, *Lasers in Surgery and Medicine*, vol. 11, 1991, pp. 419–425.
Measurement of the axial eye length and retinal thickness by laser Doppler interferometry (LDI) by C. K. Hitzenberger, A. F. Fercher, and M. Juchem, *SPIE vol. 1423 Ophthalmic Technologies*, 1991, pp. 46–50.

Primary Examiner—Edward P. Westin
Assistant Examiner—Stephen Calogero
Attorney, Agent, or Firm—Michael B. Einschlag

[57] ABSTRACT

Ophthalmologic surgical microscope which is combined internally with an optical coherence tomography ("OCT") apparatus wherein auto-focusing is provided by driving a motorized internal focusing lens of the ophthalmologic surgical microscope with a signal output from the OCT apparatus. An embodiment of the inventive ophthalmologic surgical microscope includes: (a) an optical coherence tomography ("OCT") apparatus; (b) a beamcombiner for internally coupling output from the OCT apparatus into the ophthalmologic surgical microscope; and (c) a motor for moving an internal focusing lens of the ophthalmologic surgical microscope in response to a signal from the OCT apparatus, whereby the ophthalmologic surgical microscope is auto-focused.

19 Claims, 3 Drawing Sheets

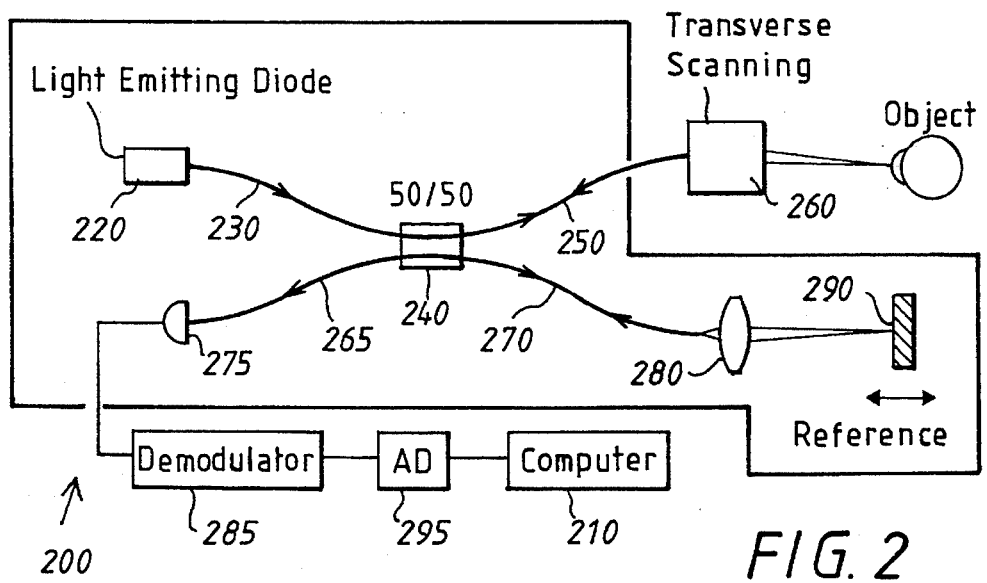
FIG. 2
FIG. 4
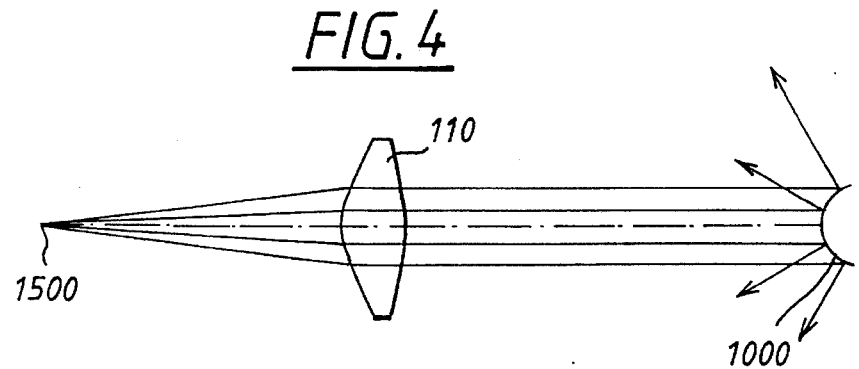
FIG. 5
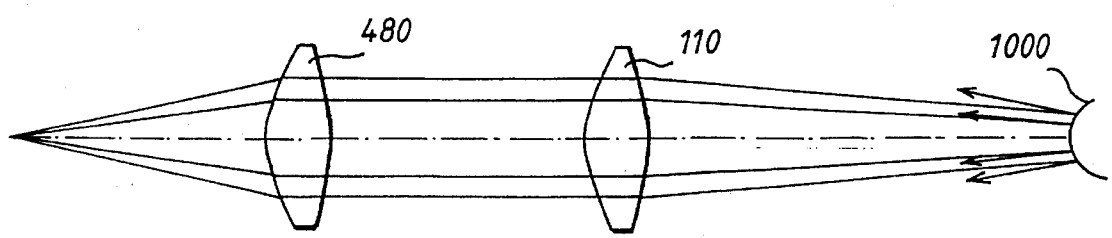

OPTICAL COHERENCE TOMOGRAPHY ASSISTED OPHTHALMOLOGIC SURGICAL MICROSCOPE

TECHNICAL FIELD OF THE INVENTION

The present invention relates to an ophthalmologic surgical microscope which includes an optical coherence tomography unit for auto-focusing on the posterior intraocular lens capsule for use, for example, in cataract surgery and for performing in-line corneal topography measurements for use, for example, in refractive surgery.

BACKGROUND OF THE INVENTION

As is well known, cataract surgery is an ophthalmologic surgical procedure for removing an opaque intraocular lens from an eye. In accordance with this surgical procedure, after the intraocular lens is removed, an artificial intraocular lens needs to be implanted to recover the patient's vision. It is desirable for an ophthalmologic surgical microscope that is used during the surgical procedure to have a capability of auto-focusing on the intraocular lens capsule during the surgical procedure, which capability is especially important after a majority of the opaque intraocular lens has been removed. After a majority of the opaque intraocular lens has been removed, small amounts of cataract residue may remain on the optically transparent intraocular lens capsule—because the intraocular lens capsule is transparent, such residue is difficult to see. As is known, it is important to completely remove such residue because any residue lea on the intraocular lens capsule will serve as a nucleus of a new cataract. Present apparatus for auto-focusing an ophthalmologic surgical microscope, such as a prior art apparatus disclosed in U.S. Pat. No.5,288,987 issued February 22, 1994, are based on detecting and measuring the intensity of light scattered from an object. However, such apparatus for auto-focusing are disadvantageous because it is difficult to focus on an optically transparent medium such as the posterior intraocular lens capsule since reflection therefrom is specular and weak.

In light of the above, there is a need in the an for an ophthalmologic surgical microscope which can auto-focus on the posterior intraocular lens capsule for use in cataract surgery.

As is well known, refractive surgery is a surgical procedure that has, as its primary objective, correction of an ametropia by making incisions in a cornea to change the refractive power of the cornea. Surgical manipulation of corneal shape requires an accurate and precise method of measuring anterior corneal curvature from apex to limbus. At present, measurement of curvature of the center of the cornea is commonly made using a keratometer and, for more precise measurements of corneal topography, it is common to utilize photokeratoscopy or videokeratoscopy.

Current corneal topography measurement apparatus are mostly Placido-disc-based videokeratoscopes. In such an apparatus, a series of concentric rings are configured on a cone-shaped housing so that an image reflected from the cornea is virtually flat in space. Then, the configuration of tile rings is analyzed to determine the corneal topography. A prior art apparatus of this type has been described in an article entitled "New Equipment and Methods for Determining The Contour of the Human Cornea" by M. G. Townsley, *Contacto*, 11(4), 1967, pp. 72–81. Such videokeratoscopes have the following disadvantages: (a) due to the small radius of the cornea (~8 mm), a limited number of rings can be resolved on the cornea (normally, the contour which can be measured is restricted to an area which ranges from 0.8 to 11 mm in diameter on the cornea); (b) no information can be obtained between the rings; and (c) due to use of rings, in-line measurement is very difficult when used in conjunction with an ophthalmologic surgical microscope. An article entitled "Accuracy and Precision of Keratometry, Photokeratoscopy, and Corneal Modeling on Calibrated Steel; Balls" by S. B. Hannush, S. L. Crawford, G. O. Waring III, M. C. Gemmill, M. J. Lynn, and A. Nizam in *Arch. Ophthalmol.*, Vol. 107, Aug. 1989, pp. 1235–1239 provides a comparison of these prior art methods and apparatus.

Another corneal topography measurement apparatus has been developed recently by PAR Microsystem Co. The apparatus utilizes raster photogrammetry to measure a corneal topography. In this apparatus, a grid pattern is projected onto the cornea. The grid pattern is then viewed and imaged from an offset angle. Finally, corneal elevation at each of the discrete points in the grid pattern are calculated using the image of the projected grid pattern, and information relating to its geometry,. This apparatus is described in an article entitled "Intraoperative raster photogrammetry— the PAR Corneal Topography System" by M. W. Berlin, J. Cataract Refract Surg, Vol. 19, Supplement, 1993, pp. 188–192. Corneal topography measurements suffer in this apparatus because only a limited number of points in the image of the projected grid pattern can be resolved by the image optics.

As is further known, since a posterior corneal surface contributes about −14% of total corneal refractive power, in some cases, an anterior corneal topography, by itself, does not provide sufficient information for use in a refractive surgical procedure. For that reason, it becomes even more important to obtain corneal topography measurements with a precision that cannot be provided by current corneal topography measurement apparatus.

In light of the above, there is a need in the art for an ophthalmologic surgical microscope which can perform in-line, corneal topography measurements for use in refractive surgical procedures.

Recently, a new ophthalmic measurement apparatus, an optical coherence tomography ("OCT") apparatus, has been disclosed which has advantages over the above-described prior art ophthalmic measurement apparatus. An OCT apparatus uses a short coherence light source for range measurements based on the principle of white light interferometry. OCT has been proposed recently for use in several ophthalmologic applications. For example, such proposals have been made in a preprint of an article which has been submitted for publication entitled "Micron-Resolution Imaging of the Anterior Eye in Vivo with Optical Coherence Tomography" by J. A. Izatt, M. R. Hee, E. A. Swanson, C. P. Lin, D. Huang, J. S. Schuman, C. A. Puliafito, and J. G. Fujimoto, 1994, pp. 1–24. The preprint discloses an OCT apparatus which utilizes optical fiber technology and a superluminescent laser diode source, which OCT apparatus is interfaced with a slitlamp biomicroscope for imaging intraocular structures with a spatial resolution of 10–20 μ. The preprint discloses the use of the OCT apparatus to provide direct, micron-resolution measurements of (a) ocular profile dimensions, optical scattering, and structure in the cornea; (b) the anterior angle region; (c) the iris; and (d) the crystalline lens. The preprint further discloses the use of the OCT apparatus to measure: (a) anterior chamber depth, defined as a distance, along the visual axis, from the posterior corneal surface to the lens anterior capsule; (b) radius of curvature of the posterior and anterior surfaces of the cornea; (c) corneal refractive power; and (d) corneal dimensions such as thickness. The preprint still further discloses that the OCT apparatus, using an inexpensive diode laser source and a fiber optic implementation, is compatible with existing ophthalmic instrumentation. Finally, the preprint makes the following suggestions for potential clinical applications of OCT: (a) providing cross-sectional images of the entire anterior chamber for use in elucidating pathologies of the cornea, anterior angle region, and iris and for use in identifying and monitoring intraocular masses or tumors; (b) measuring anterior chamber depth, corneal curvature, and corneal refractive power; and (c) providing high resolution images showing corneal thickness variations and the distribution of scattering in corneal stroma for quantitative analysis of corneal pathologies.

SUMMARY OF THE INVENTION

An embodiment of the present invention comprises an ophthalmologic surgical microscope which is combined internally with an optical coherence tomography ("OCT") apparatus wherein auto-focusing is provided by driving a motorized internal focusing lens of the ophthalmologic surgical microscope with a signal output from the OCT apparatus. In accordance with a first aspect of the present invention, whenever a particular object in the field of view is interesting, for example, the posterior lens capsule, the OCT apparatus scans the anterior chamber of the eye, along the longitudinal axis of the eye, to provide location information relating to the particular object. Then, the OCT apparatus outputs a location signal to drive the motorized internal focusing lens to auto-focus the ophthalmologic surgical microscope on the particular object.

In accordance with a second aspect of the present invention, in-line corneal tomography measurements of the anterior chamber are obtained by using a scanning apparatus, for example, a scanning apparatus comprised of two scanning motors, to provide a raster transverse OCT scan of the cornea, in conjunction with a longitudinal OCT scan. The results of the scans are analyzed by a computer to provide the following data: (a) anterior corneal surface contours, (b) posterior corneal surface contours, and (c) the thickness of the cornea. These data are used to provide in-line, on-line monitoring of corneal refractive power during a refractive surgical procedure.

In accordance with the present invention, embodiments of the ophthalmologic surgical microscope provide eye pieces and a CCD camera for direct viewing during the surgical procedure. Advantageously, since the OCT apparatus is combined with the ophthalmologic surgical microscope internally, the working distance of the microscope objective lens is preserved.

BRIEF DESCRIPTION OF THE FIGURE

FIG. 2 shows, in pictorial form, a fiber optic embodiment of the OCT apparatus shown in FIG. 1;

FIG. 4 shows, in pictorial form, the chief rays of the OCT beam between the scanning mirrors and the eye for the embodiment shown in FIG. 1; and FIG. 5 shows, in pictorial form, the chief rays of the OCT beam between the scanning mirrors and the eye for the embodiment shown in FIG. 3.

Components which are the same in the various figures have been designated by the same numerals for ease of understanding.

DETAILED DESCRIPTION

Figure 1:
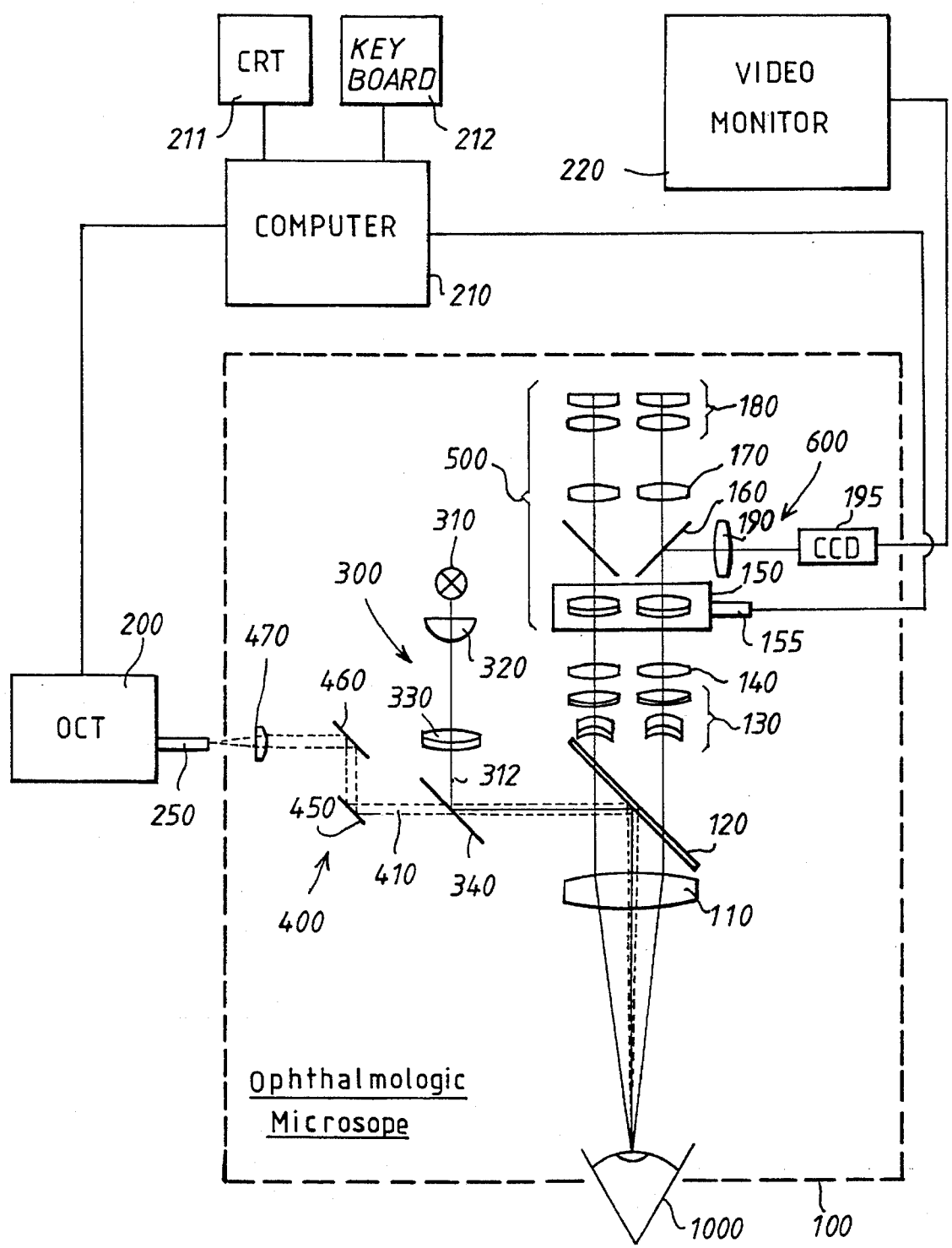
FIG. 1 shows, in pictorial form, an embodiment of the present invention which comprises an ophthalmologic surgical microscope and an optical coherence tomagraphy ("OCT") apparatus.

FIG. 1 shows, in pictorial form, an embodiment of the present invention which comprises ophthalmologic surgical microscope 100, optical coherence tomagraphy apparatus 200 ("OCT 200"), and video imaging unit 220. As shown in FIG. 1, ophthalmologic surgical microscope 100 is comprised of objective lens 110 which has a long working distance (~200 mm) for focusing on patient's eye 1000 during a surgical procedure. Beamcombiner 120 directs illumination radiation 310 from illumination path 300 and OCT radiation 410 from OCT path 400 toward objective lens 110. In a preferred embodiment, beamcombiner 120 is a hot mirror beamsplitter, i.e., a mirror which reflects radiation at higher wavelengths, for example, wavelengths higher than about 700 nm, and transmits radiation at lower wavelengths, for example, wavelengths lower than about 700 nm. As is shown in FIG. 1, ophthalmologic surgical microscope 100 further comprises optical magnification changer 130 which is set to a condition suitable for performing a particular surgical procedure (typically there are a number of groups of lenses arranged on a drum for providing varying magnifications such as, for example, 5X, 12X, 20X, and so forth). Radiation impinging upon optical magnification changer 130 is collimated.

Ophthalmologic surgical microscope 100 further comprises: (a) relay lenses 140 which take collimated radiation output from optical magnification changer 130 and form an intermediate image of an object, for example, eye 1000; and (b) internal focusing lenses 150 which are used to focus on the intermediate image of the object formed by relay lenses 140 and provide a collimated beam (internal focusing lenses 150 move up and down along viewing path 500 to provide an opportunity for internal focus adjustment).

After passing through internal focusing lenses 150, radiation is collimated and beamsplitter 160 couples a portion of the collimated radiation into optical path 600 for obtaining a video image. The video image is obtained by use of video lens 190, CCD camera 195, and video monitor 220. As those or ordinary skill in the art can readily appreciate, although the use of a single CCD camera is shown, it is within the spirit of the present invention that embodiments may be fabricated utilizing two beamsplitters, i.e., beamsplitter 160 and a similarly placed beamsplitter, to provide stereoscopic viewing through two CCD cameras.

Lastly, tube lenses 170 focus collimated radiation passed through beamsplitters 160 at an object plane of eye pieces 180. Eye pieces 180 then provide collimated output which is focused by a viewer's eyes. Since the above-described viewing path 500 is binocular, stereoscopic viewing can be obtained.

As shown in FIG. 1, illumination path 300 is comprised of: (a) incandescent light source 310; (b) condenser lens 320 for collecting radiation output from light source 310; and (c) image lens 330 for filling the entrance pupil of objective lens 110 with the filament of incandescent light source 310. Beamcombiner 340 combines OCT beam 410 with illumination radiation 310 from illumination path 300. In a preferred embodiment, beamcombiner 340 is a cold mirror beamsplitter, i.e., a mirror which reflects radiation at lower wavelengths, for example, wavelengths less than about 700 nm, and transmits radiation at higher wavelengths, for example, wavelengths higher than about 700 nm.

FIG. 2 shows, in pictorial form, a fiber optic embodiment of OCT apparatus 200. As shown in FIG. 2, OCT apparatus 200 comprises CW radiation source 220, for example, a superluminescent laser diode having an output centered substantially at 850 nm. Output from source 220 is coupled into optical fiber 230 and is separated into two beams by 50/50 coupler 240. The output from 50/50 coupler 240 is coupled into optical fibers 250 and 270, respectively. The output from fiber 270 is imaged by lens 280 onto reference mirror 290 and output from fiber 250 is directed to transverse scanning mechanism 260. The output from transverse scanning mechanism 260 is directed to impinge upon an object in a manner to be described in detail below. Then, radiation reflected from the object is coupled back into fiber 250 and superimposed by 50/50 coupler 240 with radiation reflected from reference mirror 290 and coupled back into fiber 270. Superimposed radiation output from 50/50 coupler 240 is coupled into fiber 265. As is known, there is interference between radiation reflected from the object and radiation reflected from reference mirror 290 if the optical path difference is smaller than the coherence length of radiation source 220. Reference mirror 290 is moved with a substantially constant velocity by means which are well known to those of ordinary skill in the art (not shown) and, as a result, the interference is detected as a periodic variation of a detector signal obtained by photodetector 275, the periodic variation having a frequency equal to a Doppler shift frequency which is introduced by moving reference mirror 290 with the constant velocity. The output from photodetector 275 is demodulated by demodulator 285, the demodulated output from demodulator 285 is convened to a digital signal by analog-to-digital converter 295 (A/D 295), and the output from A/D 295 is applied as input to computer 210 for analysis. The interference signal vanishes as soon as the optical path difference between radiation reflected from the object and radiation reflected from reference mirror 290 becomes larger than the coherence length of source 220. As shown in FIG. 1, the output from OCT apparatus 200 over fiber 250 is coupled into OCT path 400, which OCT path 400 includes a transverse scanning mechanism which will described below. As described above, in the embodiment shown in FIG. 1, OCT beam 410 has a wavelength centered about 850 nm and beamsplitter 120 is coated with a dichroic coating so that radiation from OCT path 400 can be continuously scanned during a surgical procedure without interruption of viewing by ophthalmologic surgical microscope 100.

In accordance with the present invention, there are two configurations utilized to provide transverse scanning. In the first configuration used to provide transverse scanning, as shown in FIG. 1, scanning mirrors 450 and 460 are orthogonally mounted, galvanometer driven scanning mirrors which are mounted on a pair of motors (not shown) and lens 470 collimates radiation output from fiber 250. The scanning motors are operated under the control of computer 210 in a manner which is well known to those of ordinary skill in the art. In the first configuration, scanning mirrors 450 and 460 are located close to the back focus of objective lens 110. FIG. 4 shows, in pictorial form, the chief rays of OCT beam 410 between scanning mirrors 450 and 460 and eye 1000 in the first configuration. As shown in FIG. 4, back focus 1500 of objective lens 110 is close to scanning mirrors 450 and 460 and the chief rays of OCT beam 410 are parallel to the optical axis in object space, i.e., the region between objective lens 110 and eye 1000. As one can readily see from FIG. 4, radiation reflected from the outer rim of the cornea of eye 1000 will be directed away from a return path to OCT apparatus 200 due to the large angle of incidence of the radiation on the cornea.

Figure 3:
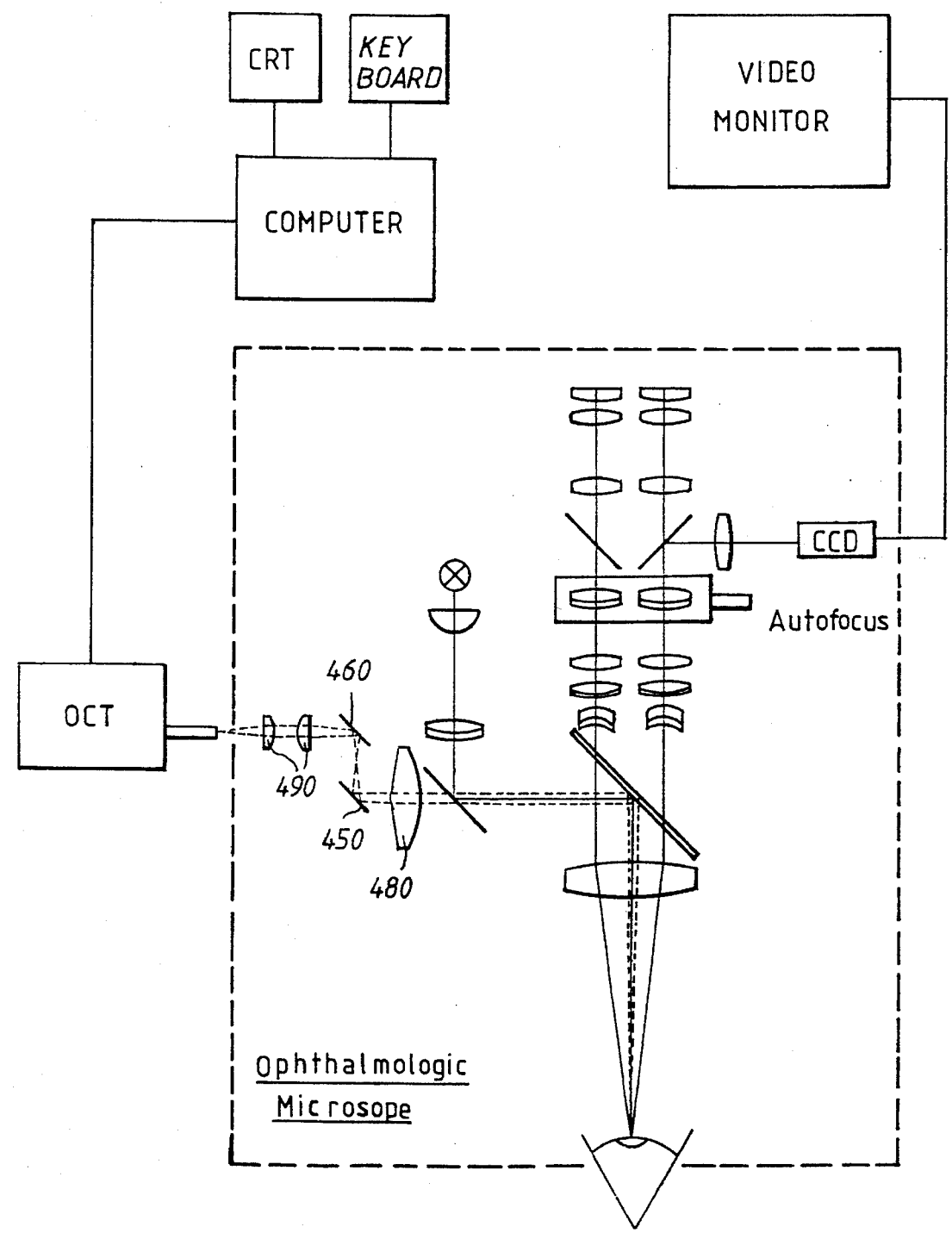
FIG. 3 shows, in pictorial form, a preferred embodiment of the present invention which comprises an ophthalmologic surgical microscope and an OCT apparatus.

The second configuration used to provide transverse scanning is illustrated in FIG. 3. As shown in FIG. 3, relay lens 490 is used to transfer the OCT point source from fiber 250 to an intermediate image which is located between scanning mirrors 450 and 460 and scanning mirrors 450 and 460 are located very close to the back focus of scanning lens 480.

FIG. 5 shows, in pictorial form, the chief rays of OCT beam 410 between scanning mirrors 450 and 460 and eye 1000 in the second configuration. As shown in FIG. 5, the chief rays of the scanning beam are parallel in relay space, i.e., the space between scanning lens 480 and objective lens 100 and the chief rays are focused close to the center of curvature of the cornea of eye 1000. Since OCT beam 410 is focused at the center of curvature of the cornea, it is normal to the surface thereof and the reflected beam is retroreflected into the return path. As a result, in the second case, the maximum signal strength is obtained everywhere on the cornea and the embodiment shown in FIG. 3 is the preferred embodiment of the present invention.

In accordance with a first aspect of the present invention, OCT unit 200, in accordance with instructions from computer 210, scans the anterior chamber of eye 1000, along the longitudinal axis of the eye, in a manner known in the art to provide location information relating to a particular object, for example, the posterior intraocular lens capsule. The output from computer 210 may be displayed on CRT 211 wherein various features obtained by the OCT longitudinal scan are made apparent by a display, for example, of signal strength as a function of location. Since the position of the posterior ocular lens is well known, it can readily be identified by a trained observer. Then, user input to computer 210 by means, for example, of keyboard 212 and/or a mouse (not shown), is used to specify a range of locations of the longitudinal scan to use for auto-focusing. In response to the user input, computer 210 chooses a location which produces a signal strength maximum within the specified range of locations and determines an appropriate position of internal focusing lens 150 to achieve proper focus on the location providing the signal strength maximum. Then, computer 210 sends an appropriate signal to motor 155 to move internal focusing lens 150 to the appropriate position. In addition to identifying signal maxima within a specified range of location, computer 210 can perform the auto-focusing by automatically locating signal strength maxima on the basis of a signal exceeding a predetermined threshold.

In accordance with a second aspect of the present invention, OCT unit 200 and scanning mirrors 450 and 460, in accordance with instructions from computer 210, provide a raster, transverse OCT scan of the cornea in conjunction with a longitudinal OCT scan, all in a manner known in the art. The results are analyzed by computer unit 210 to obtain corneal topography measurements such as: (a) anterior corneal surface contours, (b) posterior corneal surface contours, and (c) the thickness of the cornea. These data are used to provide on-line monitoring of corneal refractive power during a refractive surgical procedure. In one embodiment of this aspect of the present invention, thresholds are input to computer 210 for the purpose of identifying signals maxima corresponding to predetermined surfaces in the chamber of the eye. Then, computer 210 makes a correspondence between signals having levels above the maxima with the predetermined surfaces and captures the spatial coordinates of the surfaces in space from the longitudinal scan position and from the position of the OCT beam in the raster scan. These values in space are stored in computer 210. The thickness of the cornea is determined from the spatial difference between signal peaks produced by the posterior and anterior corneal surface during a longitudinal scan and the well known optical properties of the cornea, such as, for example, index of refraction. When the raster scan is completed, computer 210 performs a fit of the spatial coordinates of the surfaces to provide posterior and anterior corneal surface contours. Then, the surface contours are utilized to provide a measure of the curvature of the posterior and anterior surfaces of the cornea and, from them, a measure of corneal refractive power.

Those skilled in the art will recognize that the foregoing description has been presented for the sake of illustration and description only. As such, it is not intended to be exhaustive or to limit the invention to the precise form disclosed. For example, modifications and variations are possible in light of the above teaching which are considered to be within the spirit of the present invention. Thus, it is to be understood that the claims appended hereto are intended to cover all such modification and variations which fall within the true scope and spirit of the invention.

What is claimed is:

1. Ophthalmologic surgical apparatus for examining an object which comprises:

an ophthalmologic surgical microscope;

an optical coherence tomography (OCT) apparatus;

means for internally coupling optical output from the OCT apparatus into the ophthalmologic surgical microscope so that it impinges upon the object and for coupling at least a portion of the optical output which is reflected from the object into the OCT apparatus;

in response to the at least a portion of the optical output, the OCT apparatus outputting detection signals; and analysis means for analyzing the detection signals output from the OCT apparatus to identify and locate one or more features of the object; the analysis means further comprising means responsive to a location of at least one of the one or more features for moving internal focusing means of the ophthalmologic surgical microscope so that the ophthalmologic surgical microscope is focused on one of the one or more features.

2. The ophthalmologic surgical apparatus of claim 1 wherein the means for internally coupling comprises:

raster scanning means for raster scanning the optical output from the OCT apparatus;

relay lens means for transferring the optical output from the OCT apparatus to an intermediate image which is disposed within the raster scanning means; and scanning lens means for transferring the intermediate image to an objective lens means of the ophthalmologic surgical microscope wherein the intermediate image is located close to a back focus of the scanning lens means.

3. The ophthalmologic surgical apparatus of claim 2 wherein the scanning lens means is disposed so that chief rays of scanned output from the raster scanning means are substantially parallel between the scanning lens means and the objective lens means of the ophthalmologic surgical microscope.

4. The ophthalmologic surgical apparatus of claim 3 wherein the raster scanning means comprises orthogonally mounted mirrors.

5. The ophthalmologic surgical apparatus of claim 2 wherein the analyzing means further comprises:

means: (a) for causing the OCT apparatus to generate optical output which produces the detection signals to identify and locate the one or more features of the object along a longitudinal axis which extends into the object; (b) for identifying and locating the one or more features of the object along the longitudinal axis; and (c) for sending an auto-focus signal to motor means for driving the internal focusing means of the ophthalmologic surgical microscope so that it is focused on one of the one or more features.

6. The ophthalmologic surgical apparatus of claim 5 wherein the identifying and locating means comprises: (a) means for displaying representations of the detection signals; (b) means for receiving user input; and (c) means, in response to the user input, for identifying at least one of the one or more features of the object and for locating the at least one of the one or more features of the object.

7. The ophthalmologic surgical apparatus of claim 5 wherein the identifying and locating means comprises means for identifying at least one of one or more maxima of the detection signals output from the OCT apparatus and for locating the at least one of the one or more features from the identification of the at least one of the one or more maxima.

8. The ophthalmologic surgical apparatus of claim 7 wherein the identifying and locating means further comprises means for determining a distance between pairs of the one or more features.

9. An ophthalmologic surgical apparatus for examining an eye which comprises:

an ophthalmologic surgical microscope;

an optical coherence tomography (OCT) apparatus;

means for internally coupling optical output from the OCT apparatus into the ophthalmologic surgical microscope so that it impinges upon the eye and for coupling at least a portion of the optical output which is reflected from the eye into the OCT apparatus;

wherein the internal coupling means comprises raster scanning means for raster scanning the optical output from the OCT apparatus;

in response to the at least a portion of the optical output, the OCT apparatus outputting detection signals; and analysis means: (a) for causing the OCT apparatus to scan a chamber of the eye along a longitudinal axis which extends into the eye; (b) for analyzing the detection signals output from the OCT apparatus to identify and locate one or more surfaces of the chamber; and (c) for providing a contour map of the one or more surfaces of the chamber.

10. The ophthalmologic surgical apparatus of claim 9 wherein the analysis means for analyzing detection signals comprises means: (a) for detecting one or more maxima of the detection signals; (b) for associating the one or maxima with the one or more surfaces of the chamber; and (c) for providing the contour map of the one or more surfaces.

11. The ophthalmologic surgical apparatus of claim 10 wherein the analysis means further comprises means for determining a distance between at least two of the one or more surfaces.

12. The ophthalmologic surgical apparatus of claim 10 wherein the analysis means further comprises means for determining a radius of at least one of the one or more surfaces.

13. The ophthalmologic surgical apparatus of claim 10 wherein the analysis means further comprises means for displaying the contour map of the one or more surfaces.

14. The ophthalmologic surgical apparatus of claim 9 wherein the means for internally coupling further comprises:

relay lens means for transferring the optical output from the OCT apparatus to an intermediate image which is disposed within the raster scanning means; and scanning lens means for transferring the intermediate image to an objective lens means of the ophthalmologic surgical microscope wherein the intermediate image is located close to a back focus of the scanning lens means.

15. The ophthahnologic surgical apparatus of claim 14 wherein:

the analysis means for analyzing detection signals comprises means: (a) for detecting one or more maxima of the detection signals; (b) for associating the one or maxima with one or more surfaces of the chamber; and (c) for providing the contour map of the one or more surfaces.

16. The ophthalmologic surgical apparatus of claim 15 wherein:

the analysis means further comprises means for determining a distance between at least two of the one or more surfaces.

17. The ophthalmologic surgical apparatus of claim 15 wherein:

the analysis means further comprises means for determining a radius of at least one of the one or more surfaces.

18. The ophthalmologic surgical apparatus of claim 15 wherein:

wherein the analysis means further comprises means for displaying the contour map of the one or more surfaces.

19. The ophthalmologic surgical apparatus of claim 15 wherein:

the analysis means further comprises means for determining a measure of curvature of a posterior and an anterior surface of a cornea and, from them, a measure of corneal refractive power.

* * * * *